United States Patent [19]

Gerkin et al.

[11] Patent Number: 5,364,924

[45] Date of Patent: Nov. 15, 1994

[54] SUBSTITUTED UREAS CONTAINING CYCLIC AMINES AS CHAIN EXTENDERS IN POLYMERIC SYSTEMS

[75] Inventors: Richard M. Gerkin, Cross Lanes; Forest A. Richey, Jr., Charleston, both of W. Va.

[73] Assignee: OSi Specialties Inc., Danbury, Conn.

[21] Appl. No.: 40,642

[22] Filed: Mar. 31, 1993

[51] Int. Cl.$^5$ .............................................. C08G 18/32
[52] U.S. Cl. ...................................... 528/73; 528/341; 528/406; 540/484; 540/598; 540/603; 540/607; 540/612; 544/357; 544/370; 544/406; 548/312.7
[58] Field of Search .................. 528/73, 341, 406; 540/484, 598, 603, 607, 612; 544/357, 370; 548/312.7

[56] References Cited

U.S. PATENT DOCUMENTS

| | | | |
|---|---|---|---|
| 4,007,156 | 2/1977 | Ramey | 524/100 |
| 4,007,157 | 2/1977 | Ramey | 524/100 |
| 4,782,071 | 11/1988 | Butler | 514/353 |

FOREIGN PATENT DOCUMENTS 61-176569  8/1986  Japan.
61-176578  8/1986  Japan.

*Primary Examiner*—John Kight, III
*Assistant Examiner*—R. F. Johnson
*Attorney, Agent, or Firm*—Andrew S. Reiskind

[57] ABSTRACT

Diamino ureas having the formula

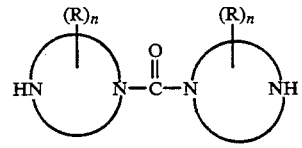

wherein each ring is saturated and includes 3-5 carbon atoms and n alkyl substituents R of 1-4 carbon atoms each and n for each ring is 1-4, a method of using these materials as chain extending agents in the manufacture of poly(urethane/urea)s or polyureas, and polymers having at least one constituent unit derived from such diamino ureas are claimed.

5 Claims, No Drawings

SUBSTITUTED UREAS CONTAINING CYCLIC AMINES AS CHAIN EXTENDERS IN POLYMERIC SYSTEMS

FIELD OF THE INVENTION

This application deals with chain extenders for polymers, and more particularly, with substituted ureas containing cyclic amines as such materials. The preferred ureas are dipiperazinyl ureas.

BACKGROUND OF THE INVENTION

Polyurethanes are prepared by reacting a compound which contains at least two reactive hydrogen atoms with a polyisocyanate. The active hydrogen-containing compound is typically a polyether or polyester polyol, but may also be a polyamine containing primary or secondary amino functionalities produced by replacing the hydroxyl functionalities of a polyol with amino groups. Both the active hydrogen-containing compound and the polyisocyanate contain at least two reactive functionalities. The polyisocyanate is generally employed in a slight molar excess relative to the total amount of the active hydrogen-containing materials in the composition. By appropriate selection of the particular active hydrogen-containing materials and the particular polyisocyanates, polymers having a wide variety of properties may be produced.

The range of properties of the resultant polymers may be extended by including in the reaction mixture one or more additional active hydrogen-containing compounds, which are generally referred to in the art as "chain extenders." Chain extenders are isocyanate-reactive materials possessing at least two active hydrogen atoms, and having molecular weights generally less than about 400. The reactive functional groups of chain extenders are generally primary or secondary hydroxyl groups, or primary or secondary amines.

Chain extenders containing hydroxyl groups are frequently somewhat slow to react with the polyisocyanate, and require one or more catalysts to achieve a sufficiently fast reaction. Such catalysts are typically organometallics such as dibutyl tin dilaurate and other similar materials known to those skilled in the art.

The residues of metal-containing catalysts can cause thermal instability in the ultimate polymer. Another potential difficulty with hydroxyl-containing chain extenders is that some of these have a limited solubility in the polyol employed as the primary active hydrogen-containing compound of the composition, thus limiting the amount of chain extender which can be used in the formulation.

Amine-containing chain extenders generally react more rapidly than the corresponding hydroxyl-containing materials, but sometimes react too fast, and in addition, may impart an odor to the resultant polymeric product.

Typical chain extenders known to the art are compounds such as ethylene glycol, 1,4-butanediol, diethylene glycol, ethylenediamine, hydrazine, isophoronediamine, diethyltoluenediamine, and methylene-bis(orthochloroaniline). Such chain extenders find application not only in the field of polyurethane and polyurea chemistry, but also in various other polymeric systems such as epoxides and polyamides, for example.

Diamines such as dipiperazinyl urea and 1,2-bis(-piperazinyl)ethanedione have been reported to be useful for the preparation of certain pharmaceutical materials, but have not apparently been suggested as chain extenders in polymeric systems. See Derwent Abstract 86-248748/38.

It is understood by those skilled in the art that the reaction between a polyol and a polyisocyanate produces a polyurethane, a reaction between a polyamine and a polyisocyanate produces a polyurea, and a reaction involving a polyol, a polyisocyanate, and a polyamine chain extender produces a poly(urethane/urea).

The art is always interested in finding new chain extender materials which possess adequate reactivity with polyisocyanate and produce polymers having good physical properties, in particular, improved hardness and modulus. Such new chain extenders are the subject of the present application.

SUMMARY OF THE INVENTION

The present invention relates to diamino ureas having the formula

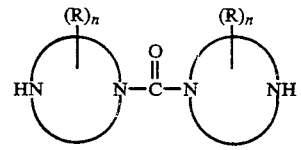

wherein each ring is saturated and includes 3–5 carbon atoms and n alkyl substituents R of 1–4 carbon atoms each, and n for each ring is 1–4.

Such materials are useful as chain extenders in polymeric systems. More particularly, the chain extenders of the present invention can be used to prepare poly(urethane/urea) polymers with very good physical properties, including improved hardness and modulus relative to prior art materials. They are also useful in other polymeric systems such as epoxides and polyamides.

The invention also relates to a process for making a poly(urethane/urea) or polyurea which comprises the following steps:

a) combining:
   i) an isocyanate-reactive material containing at least two active hydrogen atoms;
   ii) a polyisocyanate; and
   iii) a diamino urea having the formula

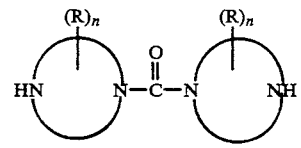

wherein each ring is saturated and includes 3–5 carbon atoms and n substituents R of 1–4 carbon atoms each, and n for each ring is 1–4; and b) effecting polymerization of reagents i, ii, and iii to produce polymer.

The present invention also includes polymers having at least one constituent unit having the formula

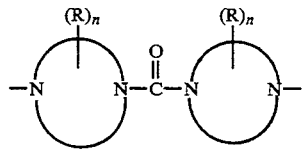

wherein each ring is saturated and includes 3–5 carbon atoms and n substituents R of 1–4 carbon atoms each, and n for each ring is 1–4.

DETAILED DESCRIPTION

The diamino urea compounds of the invention possess at least one substituent group R on each ring, preferably contain 2 to 3 such substituents per ring, and most preferably contain 2 substituents R per ring. The substituents R are preferably located adjacent to the secondary nitrogen atoms. Substituents R are preferably methyl or ethyl groups, and are most preferably methyl groups. The most preferred diamino urea of the invention is bis-(3,5-dimethylpiperazinyl)urea.

These materials are made by reacting the appropriate cyclic diamines with a material such as diphenylcarbonate, urea, a substituted urea such as carbonyldiimidazole, or phosgene. Those skilled in the art will also appreciate that there are other synthetic routes.

The substituted cyclic diamine starting materials are either commercially available or within the skill of the art to prepare. For example, six-membered cyclic diamines such as substituted piperazines are commercially available, and routes to various other substituted cyclic diamines containing five and seven ring atoms are known. Thus, for example, 2-ethylimidazoline has been reported by Murahashi, et al. in J. Am. Chem. Soc., 105, 5002–5011 (1983); 4,5-diethyl-4,5-dimethylimidazoline has been reported by White and Greene, J. Am. Chem. Soc., 100, 6760 (1978); 2-methylhexahydro-1,4-diazepin has been reported by Yakugaka Zasshi, 97, 1299–1304 (1977); 2,2-dimethyl homopiperazine and cis 5,7-dimethylhexahydro-1,4-diazepin have been reported by McDougall and Malik in J. Chem. Soc., 2044–2048 (1969).

The process for producing a poly(urethane/urea) or polyurea using the chain extenders of the invention may be carried out in any of the ways known to the art for preparing such compounds, the presently claimed process differing from processes of the prior art only in the use of the particular chain extenders of this invention.

One method of carrying out the polymerization reaction is the "one shot" process, in which the reactive hydrogen-containing starting material, the chain extender, and any required polymerization catalyst are combined to form a first mixture, and this mixture is then combined with the polyisocyanate and the resulting reaction mixture is allowed to cure.

A second process for carrying out the polymerization reaction is first to form a prepolymer by reacting an active hydrogen-containing material, such as the polyol, and the polyisocyanate to form an isocyanate-terminated prepolymer, and then to react this with the chain extender to produce the final polymeric product.

It is important to employ the correct stoichiometry in carrying out the polymerization reaction. Typically, the total number of isocyanate groups will be greater than or equal to the sum of the active hydrogen-containing groups in the reacting system. This concept is expressed in the "isocyanate index", which is usually somewhat greater than 100. In other words, if the isocyanate index is greater than 100, there is an excess of isocyanate groups relative to the active hydrogen-containing groups in the reacting system.

In the preparation of epoxies or polyamides the diamino urea compounds of the invention are allowed to react with epoxy resins (to give epoxies) or dicarboxylic acids or acid chlorides (to give polyamides) to form those corresponding polymers.

The diamino urea compounds of the invention are employed in polyurea or polyurethane ureas at levels from about 1% to about 30% by weight. In polyamides use levels of 50% by weight or more are not uncommon. Similarly high levels could be used in epoxies. However, more normal levels are 10% to about 40% by weight.

Curing of the reaction mixture is typically carried out at a temperature between 40° C. and 100° C., the actual temperature depending on the particular ingredients being employed, their ratios, etc.

The reagents employed in the polymerization reaction are, with the exception of the chain extending materials of the present invention, all well known to those skilled in this art. These reagents will be discussed briefly in the paragraphs below.

The isocyanate-reactive materials used to prepare polyurethanes or polyurethane ureas contain at least two active hydrogen atoms per molecule, as determined by the Zerewittinoff method. There are four classes of such materials:

(1) Polyether polyols. These materials are the products of reaction between a simple starter molecule such as ethylene glycol, propylene glycol, glycerin, pentaerythritol, trimethylolpropane, sucrose, or sorbitol, and a cyclic ether such as ethylene oxide, propylene oxide, mixtures of ethylene oxide and propylene oxide, or tetrahydrofuran.

Also included within this class of active hydrogen-containing materials are polymer polyols, which are compositions in which a polymer has been formed in a polyether polyol medium. The polymers employed in these systems may be polymers of unsaturated monomers such as acrylonitrile or styrene, and also may be copolymers or terpolymers of such monomers. They may additionally be polyureas prepared from reaction of polyisocyanates and diamines, or polyurethanes prepared by reaction of polyisocyanates and polyalkanol amines such as triethanol amine.

(2) Amine terminated polyethers. These are based on the polyether polyols discussed above, in which the terminal hydroxl groups have been replaced by primary or secondary amino functionalities. Primary amine terminated polyethers are commercially available as the Jeffamines ™ of the Jefferson Chemical Company.

(3) Polyester polyols. These are polyalkylene glycol esters such as polybutylene terephthalate or adipate, or caprolactone polyesters. Polyalkylene glycol adipates are prepared by condensation polymerization of the alkylene glycol and the corresponding diester or diacid. An example would be 1,4-butanediol plus adipic acid to form the "butanediol adipate." The condensation chemistry is carefully controlled to insure that these polyols contain terminal hydroxyl groups. Caprolactone polyesters are prepared by ring opening polymerization of caprolactone monomer with a glycol such as diethylene glycol or ethylene glycol.

(4) Polycarbonates, such as poly(1,6-hexanediol)carbonate. Such polycarbonates are prepared by condensation of phosgene or alkylene glycol carbonates, e.g., dimethyl carbonate, with alkylene glycols such as 1,6-hexanediol. As in ester chemistry, this chemistry is controlled to insure that these polycarbonates contain terminal hydroxyl groups.

The polyisocyanates employed in the polymerization reaction are generally aromatic polyisocyanates such as toluene diisocyanate, naphthalene diisocyanate, 1,4-isocyanatobenzene, and 4,4'-diphenylmethane diisocyanate and its derivatives.

The polyisocyanates may also be aliphatic materials such as isophorone diisocyanate, tetramethylxylylene diisocyanate, bis(cyclohexylmethane)diisocyanate, 1,6-hexane diisocyanate and its derivatives, and 1,4-isocyanatocyclohexane.

Catalysts which may be employed in the polymerization reaction are generally not required when all of the active hydrogen-containing compounds are amines. On the other hand, if the active hydrogen-containing compounds are alcohols, a catalyst is generally required to provide reasonable reaction rates. Even here, however, it is not absolutely essential that a catalyst be employed. Examples of typical catalysts are amines such as triethylene diamine, bis(dimethylamino)ethyl ether, dimethylcyclohexylamine, pentamethyldiethylenetriamine, and triethylamine. Metallic catalysts such as stannous octoate, dibutyl tin dilaurate or diacetate, and phenylmercuric propionate are particularly desirable for promoting the reaction between hydroxyl groups and isocyanate groups.

The polymers produced using the chain extending agents of the present invention are generally tough and abrasion resistant materials which find use as cast parts such as solid tires, molded gears, and bushings, as well as other molded parts such as fenders or bumpers of automotive vehicles. Softer polymers containing the chain extenders of the invention find use as components of sealants.

The chain extending agents of the invention are not restricted to use in polyurethanes, polyureas, or poly(urethane/urea) materials, but also may be employed in other polymeric systems such as polyamides and epoxides, among others. In forming polyamides, the diamino ureas of the invention are reacted with appropriate dicarboxylic acids, acid chlorides, or anhydrides. For very high molecular weight polyamides, one equivalent each of the diamino urea and the dicarboxylic acid or acid chloride is the preferred ratio of reactants. In forming epoxides, the diamino urea reacts with an epoxy resin containing multiple epoxy groups. The ring opening addition reaction to the epoxy group results in crosslinking. Typically, the ratio of diamino urea to epoxy resin is not critical to performance of the cured polymer. The ratio can be varied to affect different properties in the cured system.

Glossary

Amine A is a secondary amine-terminated polyether having a total amine content of 0.449 meq/g and an equivalent weight of 2226.

Amine B is UNILINK TM 4200, which is a commercially available aromatic diamine chain extender sold by UOP.

CDI stands for carbonyldiimidazole.

DBTDL stands for dibutyl tin dilaurate catalyst.

DETDA stands for diethyl toluene diamine, a commercial diamine chain extender available from Miles Corporation or Ethyl Corporation.

DMP stands for 2,6-dimethyl piperazine.

DMPU stands for bis(3,5-dimethylpiperazinyl)urea.

DPC stands for diphenylcarbonate.

IPDI stands for isophorone diisocyanate, which has an equivalent weight of 111.

Polyol 1 stands for ARCOL® 24-32, a commercial polyether polymer polyol which has a hydroxyl number of 32.4 mg KOH/g and an equivalent weight of 1731.5, available from Arco chemical company.

EXPERIMENTAL

Preparation of bis(3,5-dimethylpiperazinyl)urea (DMPU) from 2,6-dimethylpiperazine (DMP) and diphenylcarbonate (DPC)

Step 1: A mixture of 2.85 g (0.025 mole) of DMP, 6.43 g (0.03 mole) of DPC, and 20 ml of o-xylene where heated overnight at 152°–153° C. Subsequent gas chromatographic analysis showed that all of the DMP had been consumed and a new material, presumed to be an intermediate carbamate, was present. The flask was equipped for distillation and heated to 204° C. at atmospheric pressure, then cooled and stripped under vacuum with pressures as low as 2 mm Hg and temperatures from 120° to 132° C. to remove phenol and xylene. After this operation, the flask contained the carbamate and a trace of phenol.

Step 2: An additional 2.85 g of DMP were added to the flask contents and the mixture was heated. Phenol was removed as above, resulting in a product mixture containing both the carbamate and product DMPU. The mixture was taken as a residue product.

Preparation of bis(3.5-dimethylpiperazinyl)urea (DMPU) from 2,6-dimethylpiperazine (DMP) and urea A mixture of 10 g (0.088 mole) of DMP and 2.4 g (0.040 mole) of urea was placed in a 100 ml flask supplied with a heating mantle, thermometer, reflux condenser, nitrogen atmosphere, magnetic stirrer, and teflon covered stirring bar. This mixture was stirred and heated at temperatures from 160° to 200° C. for 3 hours and analyzed by gas chromatography, which showed a peak having the same retention time as authentic bis(3,5-dimethylpiperazinyl)urea.

Preparation of bis(3,5-dimethylpiperazinyl)urea (DMPU) from 2,6-dimethylpiperazine (DMP) and carbonyldiimidazole (CDI)

A mixture of 63.81 g (0.559 mole) of DMP and 38.41 g (0.2369 mole) of CDI was charged to a 500 ml round bottom four-necked flask equipped with a thermometer, means for maintaining a nitrogen atmosphere, a mechanical stirrer, and a heating mantle. The mixture was stirred, heated, and held at 161° to 181° C. During five days of intermittent heating, 15.20 g (0.0937 mole) of additional CDI was added, bringing the total amount of CDI to 53.61 g (0.331 mole). At the end of this time gas chromatographic analysis revealed that the DMP had been consumed. The product was distilled, giving fractions boiling up to 177° C. at 3 mm of Hg, including some fractions which were substantially pure bis(3,5-dimethylpiperazinyl)urea, as shown by gas chromatography.

In an earlier preparation based on reaction of DMP with CDI, the product was analyzed by coupled gas chromatography/infrared spectrometry/mass spectrometry and the major product was identified as the expected bis(3,5-dimethylpiperazinyl)urea.

Preparation of Prepolymer from Isophorone Diisocyanate (IPDI) and Polyol 1

IPDI (189.9 g), polyol 1 (1000 g) and DBTDL catalyst (0.595 g) were added to a reactor under a nitrogen blanket and heated with stirring to 80° C. After an exotherm to 100° C. occurred, heating was maintained at 80° C. for 7.5 hours. The final free isocyanate content of the prepolymer was 3.84%, for an equivalent weight of 1094.

Preparation of Control Elastomer Containing No Chain Extender

In this preparation, the prepolymer of IPDI and polyol 1 prepared above was reacted with Amine A to prepare a poly(urethane/urea) elastomer. The prepolymer (36.36 g, 0.0333 eq.) and Amine A (70.0 g, 0.0315 eq.) were mixed in a paper carton and then degassed in a vacuum desiccator for 1 minute. The mixture was poured into an aluminum mold having a cavity of about 0.125×4×6 inches, the mold was fitted with a top, and the entire assembly was placed in a press whose platens were heated to 70° C. After one hour in the press, the polymer was removed from the mold and tested. The properties of the product polymer are given in Table I below.

Demonstration of Utility of Bis(3,5-dimethylpiperazinyl)urea (DMPU) as a Chain Extender in the Preparation of a Poly(urethane/urea) Elastomer DMPU (5.0 g, 0.0394 eq.) and Amine A (55.4 g, 0.0244 eq.) were added to a 150 ml beaker. The above-described prepolymer of IPDI and polyol 1 (72.28 g, 0.067 eq.) was added to a separate beaker, and both materials were heated to approximately 70° C. to facilitate dissolution of the urea derivative, then both samples were degassed in a vacuum desiccator. The temperature dropped to about 60° C., and the urea appeared to remain dissolved in the Amine A solution. The reagents were combined, mixed thoroughly, then poured into an aluminum mold which had been preheated to about 70° C. The top was placed on the mold and the assembly was heated at 70° C. in a press for one hour. The elastomer was then demolded and tested. The properties of the resulting product are given in Table I below.

Preparation of Elastomer Containing DETDA Chain Extender

Using the procedure described directly above, the DMPU was replaced by an equal number of equivalents of DETDA and the polymerization carried out. The demolded elastomer had the physical properties described in Table I.

Preparation of Elastomer Containing U4200 Chain Extender

Using the procedure described directly above, the DETDA was replaced by an equal number of equivalents of Unilink ™ 4200 and the polymerization carried out. The demolded elastomer had the physical properties described in Table I.

TABLE I

| Physical Properties of Poly(urethane/urea)s made with Various Chain Extenders | | | | |
|---|---|---|---|---|
| Property | None[a] | DETDA[b] | AMINE B[c] | DMPU[d] |
| Hardness[f] | 22 | 30 | 5 | 40 |
| Rebound (%) | — | 39 | 18 | 41 |
| Tensile Strength (psi)[g] | 280 | 280 | 152 | 700 |
| Elongation (100%)[g] | 560 | 850 | 890 | 680 |
| Modulus (100%)[g] | 45 | 53 | 12 | 103 |
| Modulus (200%)[g] | 71 | 75 | 17 | 172 |
| Gel Time (25° C., min) | 5 | 20 | 60 | 2[e] |

[a]Control.
[b]DETDA is diethyltoluene diamine.
[c]UNILINK ® 4200, an aromatic secondary diamine commercially available from UOP.
[d]bis(3,5-dimethylpiperazinyl)urea.
[e]T = 80° C.
[f]Shore D Hardness. ASTM D-2240.
[g]ASTM D-412.

The polymer containing the chain extender of the invention (DMPU) shows tensile strength and modulus values which are clearly superior to those of the control and the other polymers which contain prior art chain extenders. Its hardness and rebound values were also superior. The DETDA and Amine B chain extenders produced polymers which were too low in modulus and had poor strength properties. Amine B produced a very soft polymer.

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

We claim:

1. A process for making a poly(urethane/urea) or polyurea, comprising the following steps:
   a) combining
      i) an isocyanate-reactive material containing at least two active hydrogens;
      ii) a polyisocyanate; and
      iii) a diamino urea having the formula

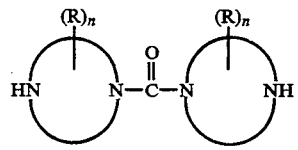

wherein each ring is saturated and includes 3–5 carbon atoms and n substituents R of 1–4 carbon atoms each, and n for each ring is 1–4; and
   b) effecting polymerization of reagents i, ii, iii to produce polymer.

2. The process of claim 1 wherein the diamino urea has the formula

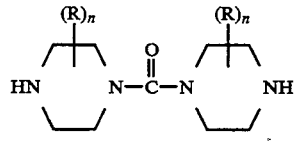

wherein each substituent R is methyl or ethyl and n is 1 or 2 for each ring.

3. The process of claim 2 wherein in said diamino urea the substituents R are located on carbon atoms adjacent to the secondary nitrogen atoms.

4. The process of claim 2 wherein said diamino urea has the formula

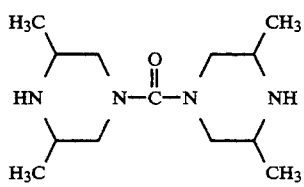
5. A polymer selected from the group consisting of polyurethane, poly(urethane/urea), polyurea, polyamide, and epoxides, having at least 1 constituent unit having the formula
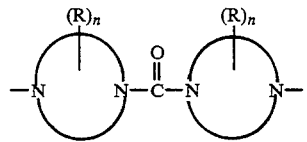
wherein each ring is saturated and includes n alkyl substituents of 1–4 carbon atoms each, and n for each ring is 1–4.
* * * * *